(12) United States Patent
Illich et al.

(10) Patent No.: US 7,006,749 B2
(45) Date of Patent: Feb. 28, 2006

(54) LASER SYSTEM WITH FIBER-BOUND COMMUNICATION

(75) Inventors: Wolfgang Illich, Wessling (DE);
Jürgen Austen, Freising (DE); Werner Hiereth, Gilching/Geisenbrunn (DE)

(73) Assignee: Dornier MedTech Laser GmbH, Munich (DE)

( * ) Notice: Subject to any disclaimer, the term of this patent is extended or adjusted under 35 U.S.C. 154(b) by 90 days.

(21) Appl. No.: 10/638,289

(22) Filed: Aug. 7, 2003

(65) Prior Publication Data
US 2004/0073202 A1     Apr. 15, 2004

(30) Foreign Application Priority Data
Aug. 7, 2002     (DE)     ............................ 102 36 175

(51) Int. Cl.
G02B 6/42     (2006.01)
G02B 6/32     (2006.01)
A61B 18/18    (2006.01)

(52) U.S. Cl. .................... 385/137; 385/33; 385/88; 606/16; 606/17; 607/93

(58) Field of Classification Search ............... 385/31, 385/88, 92, 93, 137, 147, 33; 606/16–18; 607/88, 89, 93, 94
See application file for complete search history.

(56) References Cited

U.S. PATENT DOCUMENTS

| 5,409,537 | A | 4/1995 | Poullos et al. |
|---|---|---|---|
| 5,535,399 | A | 7/1996 | Blitz et al. |
| 5,738,679 | A | 4/1998 | Daikuzono |
| 5,841,562 | A * | 11/1998 | Rangwala et al. .......... 398/139 |
| 6,086,366 | A | 7/2000 | Mueller et al. |
| 6,092,722 | A | 7/2000 | Heinrichs et al. |
| 6,377,591 | B1 | 4/2002 | Hollister et al. |
| 2002/0073082 | A1 | 6/2002 | Duvillier et al. |
| 2002/0081080 | A1 * | 6/2002 | Balle-Petersen et al. ...... 385/93 |
| 2002/0183811 | A1 * | 12/2002 | Irwin .......................... 607/94 |
| 2004/0037498 | A1 | 2/2004 | Thiele et al. |

FOREIGN PATENT DOCUMENTS

| DE | 40 25 851 C2 | 2/1993 |
|---|---|---|
| DE | 195 34 590 A1 | 3/1997 |
| DE | 196 29 646 C2 | 9/1998 |
| DE | 101 06 297 A1 | 1/2002 |

* cited by examiner

*Primary Examiner*—Sarah Song
(74) *Attorney, Agent, or Firm*—King & Spalding LLP

(57) ABSTRACT

A laser system is provided that includes a laser unit, an incoupling means for coupling the laser radiation into a light-guide, and an outcoupling means for coupling the laser radiation out from the light-guide. A data transmitting means is coupled to the incoupling means or outcoupling means and produces optical signals which are coupled into the light-guide via the incoupling means or the outcoupling means. These optical signals are received by a data receiving means at the other end of the light-guide. The laser system can be used for realizing a data communication between the hand-piece and the stationary unit of the laser system in the case of which additional cables between the hand-piece and the laser are not necessary for transmitting data.

36 Claims, 6 Drawing Sheets

LASER SYSTEM WITH FIBER-BOUND COMMUNICATION

CROSS REFERENCE TO RELATED APPLICATION

This application claims priority to co-pending German Patent Application No. 102 36 175.4, which was filed on Aug. 7, 2002 and is incorporated herein by reference.

FIELD OF THE INVENTION

The present invention generally relates to a laser system for medical applications, and more particularly, to a laser system with fiber-bound communication.

BACKGROUND OF THE INVENTION

Laser light has gained acceptance as a controllable light source not only in scientific research but also in many fields of everyday life. This is primarily due to the fact that a laser provides a monochromatic light source with coherent radiation which can be focused very well due to the small divergence. The use of lasers has become increasingly common not only in the field of telecommunications and entertainment electronics but also for treating materials and for medical purposes. In the latter field, it has been of decisive importance that a laser is an instrument permitting, on the one hand, the use of high-energy radiation for heating tissue in a precisely localized manner and for destroying endogenic calculi and, on the other hand, the use of monochromatic radiation for selectively stimulating photochemical processes. In this respect, a distinction is made between lasers used as an aid in doing a major operation and the use of lasers as an actual therapeutic method.

In the field of surgery, lasers are primarily used because of their haemostatic effect, the possibility of precise handling, and the reduction of the number of instruments in the operating field. Contact-free removal of tissue and minimum traumatizing of the surrounding tissue by force-free treatment of the tissue are essential advantages achieved by the use of a laser.

Another field of application of laser technology in medicine is the treatment of body surfaces. Lasers are here used for removing or coagulating skin and cutaneous appendages on the one hand and for treating intracutaneous vascular modifications and malformations on the other. Cutaneous tumors, for example, are nowadays preferably coagulated by means of an Nd:YAG laser or, alternatively, removed by means of a $CO_2$ laser. Non-malignant pigmentary anomalies are treated with alexandrite or argon lasers. Alexandrite lasers and pulsed Nd:YAG lasers are also used for removing tattoos and for the purpose of depilation.

Also in the field of endoscopy, lasers have become indispensable. Laser light conducted via light-guides to the location of application can here lead to a further reduction of size and thus to a higher flexibility of endoscopic operations. Due to the further development and primarily due to the miniaturization of the instruments as well as the refinement of flexible endoscopes, several new fields of application, in which conventional operations had to be performed up to now or in which the application of minimal-invasive therapies has been impossible up to now, have been opened up for the use of laser technology.

The increasing number of fields of application of laser technology in medicine resulted in the development of technically more and more progressive laser designs and corresponding system concepts, which facilitated and improved the handling of laser systems and which, in turn, opened up new fields of use.

This development of medical laser systems now continues and leads even to "intelligent" systems. German Patent Publication DE4025851 describes such an "intelligent" laser system in which reemitted radiation produced during the treatment of material by means of laser light is transmitted to a detector via a transmission system for the laser light. The detector determines the intensity of the reemitted radiation. Such a laser system can successfully be used for minimizing unintentional tissue damage, since the laser power is controlled automatically via the detection of the intensity of the reemitted radiation.

In this connection, the use of flexible, optical transmission systems for the laser radiation produced is of substantial importance, since, for applying the laser radiation to the tissue to be treated, the distance between the laser unit output and the patient has to be bridged. Hence, medical laser systems are typically composed of a stationary or mobile laser unit, beam guiding means, optical terminals, and accessories for special medical applications. For the transmission of visible laser light and the adjoining spectral regions of approx. 0.3–2.1 $\mu$m, flexible glass or silica fibers are used. In the spectral regions 0.19–0.3 $\mu$m (Eximer laser) and 3–10 $\mu$m (erbium and $CO_2$ laser), special light-guides or articulated arms with mirrors are used. Light-guides have to fulfill particularly high demands when pulsed, high-energy laser radiation is to be transmitted for the purpose of laser lithotripsy. Good handling properties and a high flexibility of these transmission systems is of decisive importance with regard to the use of the laser systems.

In the case of all application possibilities of lasers in the field of medicine, the handling properties of the laser radiation are of essential importance. Flexibility, ergonomics, and functionality are in this connection as important as safety, reliability, and precision. These are the factors that determine to a decisive extent whether the advantages of a laser can actually be utilized when carrying out the treatment in question.

In this connection, it is of essential importance how the hand-piece of a laser system, which is coupled to the laser unit output by means of an articulated arm with mirrors or by a flexible glass fiber, is user-friendly usable and operable. This includes functionalities, such as, for example, a continuous adjustment of the spot size of the laser focus. Up to now, it has been necessary to manually readjust the laser power at the laser unit after an adjustment of the spot size. More recent generations of laser systems allow an adaptation of the laser power through remote control. For this purpose, either additional electric cables from the hand-piece to the laser or RF radio transmission is/are used for transmitting data from a laser hand-piece to the laser unit. Another possibility is infrared transmission, which is either directed or diffuse. Each of these three transmission possibilities has certain specific drawbacks with respect to handiness, power consumption and effectiveness of the method, or they lead to problems as far as a worldwide approval of the laser system is concerned.

SUMMARY OF THE INVENTION

The present invention, according to exemplary embodiments described herein, provides a laser system that permits a reliable exchange of data between the hand-piece and the stationary unit. The invention takes into account the ergonomic demands that have to be fulfilled by the hand-piece, which is adapted to be easily integrated in existing laser systems without resulting in additional difficulties as far as the world-wide admission of the laser unit. The present invention is based on the finding that data can be transmitted from the hand-piece to the stationary unit of the laser by utilizing the light-guide which is used for the therapy laser.

The present invention can enable data communication between the hand-piece and the stationary unit of the laser system in the case of which additional cables are not necessary between the hand-piece and the laser, and admission procedures for a worldwide admission of the system are not influenced negatively due to RF components. Furthermore, problems with the reliability of data communication, which may arise, for example, in the case of directed or diffuse infrared transmission, can be avoided. The solution according to exemplary embodiments of the present invention additionally offers the advantage that it is adapted to be integrated in existing systems, primarily in view of the fact that it hardly interferes with the complicated optics of the laser system. In certain laser systems, existing system components can also be used for the solution according to the present invention, whereby the outlay for an integration of data transmission from the hand-piece to the stationary unit can be reduced still further.

According to an aspect of the present invention, the laser system can include a unit for producing laser radiation; an incoupling means for coupling the laser radiation produced into a light-guide, and an outcoupling means for coupling the laser radiation out from the light-guide, wherein a data transmitting means is coupled to the incoupling means or outcoupling means and produces optical signals which are coupled into the light-guide via the incoupling means or the outcoupling means and which are received by a first data receiving means at the other end of the light-guide.

According to another aspect of the invention, the laser system can include a data transmitting and a data receiving means in the incoupling means as well as in the outcoupling means so as to permit a bidirectional, optical transmission via the light-guide. The optical signals are here used for transmitting information to the hand-piece, for example, for controlling the unit for producing laser radiation, for controlling the incoupling or outcoupling means and, for controlling the laser power.

According to another aspect of the invention, the laser system can be a medical laser system, the data transmitting means coupled to the outcoupling means being here an LED or some other light source that can produce optical signals in the blue spectral region. The optical signals of the LED can be coupled out from the optical path of the laser via a mirror with a dielectric coating in the incoupling means, and they can be transmitted to a data receiving means that can also be used for detecting other optical signals, for example, for measuring reemitted radiation originating from the treatment of material by means of the laser radiation.

In accordance with yet another aspect of the present invention, the hand-piece can be provided with operating means which, when actuated, can produce electric signals and advance them to the LED provided in the hand-piece, the unit for producing laser radiation being controlled by the electric signals. This operating means can preferably be used for controlling the laser power. The hand-piece can have a modular structural design and, depending on the respective intended use of the laser, elements of the hand-piece can be added, replaced, or removed. The individual elements of the hand-piece can be provided with an identification means, which can be read optically or electronically and which can be read via a reading unit in the hand-piece when the elements are mounted to the hand-piece. The data provided by the identification means can be forwarded to the data transmitting means in the hand-piece and used for controlling the hand-piece or the unit for producing laser radiation.

These and other aspects of the invention will be described further in the detailed description below in connection with the drawings and the claims.

BRIEF DESCRIPTION OF THE DRAWINGS

The accompanying drawings are incorporated into and form a part of the specification for the purpose of explaining the principles of the invention. The drawings are not to be construed as limiting the invention to only the illustrated and described examples of how the invention can be made and used. Further features and advantages will become apparent from the following, and more particular description of the invention as illustrated in the accompanying drawings, wherein.

DETAILED DESCRIPTION OF THE EXEMPLARY EMBODIMENTS

Figure 1:
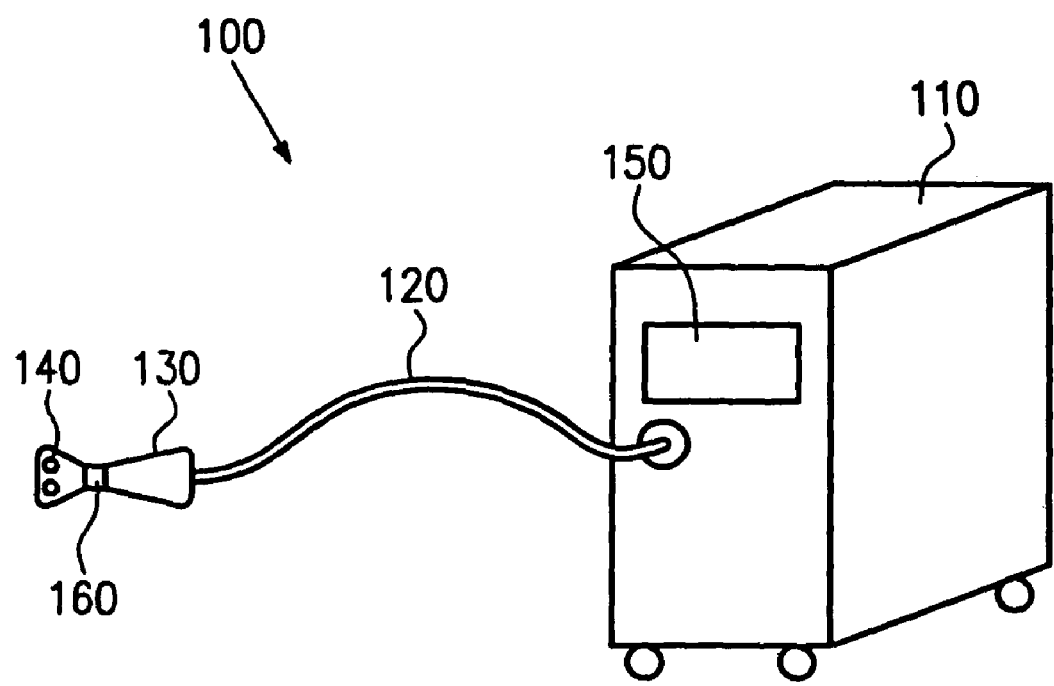
FIG. 1 shows a schematic diagram of a laser system according to exemplary embodiments of the present invention.

The illustrative embodiments of the present invention will be described with reference to the drawings, wherein like elements and structures are indicated with like reference numbers. FIG. 1 shows, on the basis of a schematic diagram, an exemplary embodiment of the present invention. The laser system 100 comprises a stationary or transportable laser unit 110 including a means for generating laser radiation, which has coupled thereto a flexible light-guide 120 connected to a hand piece 130. For producing intensive laser radiation, the laser unit 110 can be equipped with high-power laser diodes, a microoptical system for focusing the laser light produced, and a power supply. Alternatively, the laser unit can be equipped with a laser medium, a resonator, and a pumping source, as well as with a suitable power supply. In this case, diode-pumped solid-state laser media are typically used for generating the intensive laser radiation.

In addition, the laser unit 110 can include a cooling unit as well as a system controller, which can control, among other magnitudes, the power of the laser radiation and the pulse duration, as well as the frequency of the laser pulses. The laser unit 110 can have additionally integrated therein display and operating means 150 through which specific application modes and system adjustments can be chosen. Furthermore, the laser unit 110 can be provided with suitable safety means (not depicted) both for the electrical and the optical region. The system controller can be provided with suitable means which permit the laser system 100 to be controlled and adjusted via software programs. Exemplary embodiments of the invention in which software programs are exchanged for updating purposes is particularly advantageous for this purpose. In accordance with some exemplary embodiments of the present invention, the laser unit 110 can have integrated therein an output unit (not depicted) for a protocol of the system adjustments, or the laser unit 110 can be provided with an interface for an output unit.

In addition, the laser unit 110 has integrated therein an incoupling means (discussed with respect to FIGS. 3 and 5) which couples the generated laser radiation into the light-guide 120. For this purpose, the light-guide 120 is fixedly or releasably mounted in position, for example, with a precision bayonet lock, at a fixed position relative to the incoupling means. Alternatively to a precision bayonet lock, a so-called SMA connector can be used. The light-guide 120 can comprise one or a plurality of plastic, glass, or silica glass fibers. Depending on the wavelength of the laser radiation produced, doped silica glass fibers can be used as well. The light-guide 120 can be configured such that it is capable of transporting high optical powers with the least possible losses. For safety reasons, it can be provided with a suitable sheath protecting the fibers against respective mechanical loads and, in the case of fiber breakage, against an escape of laser radiation.

Similar to the laser unit 110, also the hand-piece 130 is provided with a suitable device by means of which the light-guide 120 can, fixedly or releasably, be attached to the hand-piece 130. Accordingly, the hand-piece 130 has integrated therein an outcoupling means (discussed with respect to FIGS. 2 and 4) which couples the generated laser radiation out from the light-guide 120 and transmits it, depending on the field of use of the laser system 100, to a respective outcoupling means for the laser beam in the hand-piece 130. The hand-piece 130 has for this purpose a suitable exit opening for the laser radiation. In addition, the hand-piece 130 of exemplary embodiments of the present invention typically comprises suitable operating means 140 with the aid of which certain functions of the laser unit 110 can be controlled, such as, for example, the laser power. The hand-piece 130 can additionally be provided with one or a plurality of display unit(s) through which information can be displayed and adjustments of the hand-piece 130 or of the laser unit 110 can be checked.

Figure 2:
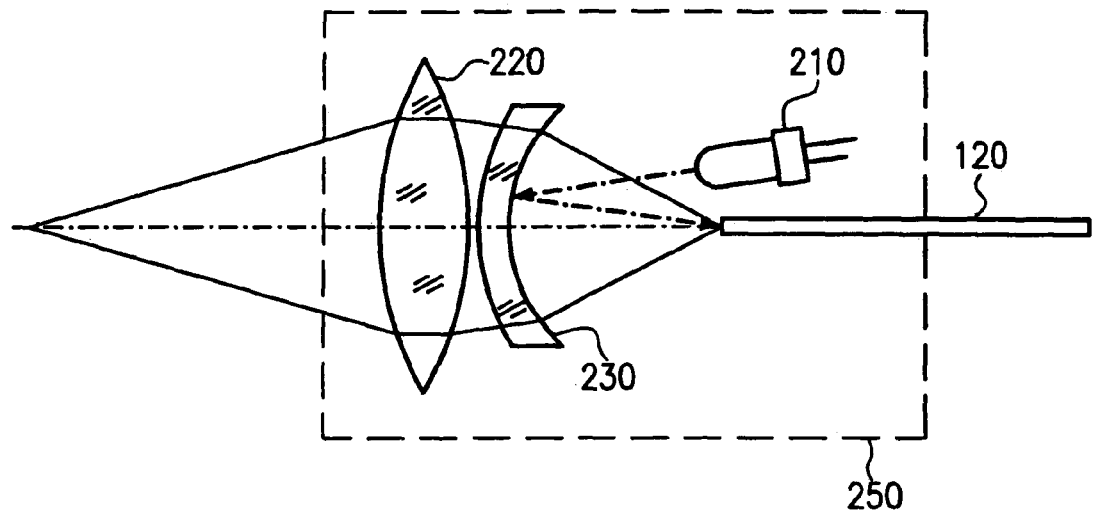
FIG. 2 shows a schematic diagram of the outcoupling means and of the light-guide according to exemplary embodiments of the present invention.

FIG. 2 shows on the basis of a schematic diagram the outcoupling means 250 of an exemplary embodiment of the present invention. The laser radiation exiting from the light-guide 120 is concentrated by means of a lens system 220 and 230 and transmitted to the outcoupling means 250 in the hand-piece 130. The outcoupling means 250 has coupled thereto a data transmitting means 210 which produces optical signals and couples these signals into the light-guide 120 via a reflection at the lens system 220, 230. The data transmitting means 210 can comprise an LED which emits optical signals in a spectral region other than the spectral region of the laser radiation. Alternatively, the data transmitting means 210 can comprise other components for producing optical signals.

For the laser unit 110 to generate high-power laser radiation in the infrared region, an LED emitting in the blue region of the spectrum can be used in accordance with exemplary embodiments of the invention, so as to guarantee a sufficient signal-to-noise ratio between the optical signals produced and the laser radiation. Alternatively, LEDs emitting in other wavelength regions, as well as other components for producing optical signals, can be used for the data transmitting means 210. The lens system 220, 230 can be provided with a dielectric coating, which is optimized in such a way that the reflection of the laser radiation will be minimized, whereby the transmission of laser radiation through the lens system 220, 230 will be maximized. Alternatively, the coating of the lens system 220, 230 can also be optimized in such a way that the highest possible reflection at the lens system 220, 230 can additionally be obtained for the spectral region of the optical signals of the data transmitting means 210. The optical signals of the data transmitting means 210 can thus be coupled into the light-guide 120 in a particularly efficient manner.

In some exemplary embodiments of the present invention, the hand-piece 130 can include mechanical displacement means coupled to a potentiometer or to electrical or optical incremental encoders. The potentiometer or the electrical or optical incremental encoders transmit, via an electronic unit, the current adjustments of the mechanical displacement means to the data transmitting means 210. In this way, for example, the distance of the hand-piece 130 to a surface and, thus, the laser spot size, can be determined, and the laser power can be readjusted accordingly. Alternatively, a distance measurement can also be carried out by using a contactless sensor instead of the mechanical displacement means in the hand-piece 130.

The hand-piece 130 can be provided with a battery or a rechargeable battery for supplying power to the electronics for the data transmitting means 210 and to the electronics required for the operating means 140. Alternatively, a capacitance-buffered power supply can be used.

The hand-piece 130 should fulfill ergonomic requirements on the one hand and, on the other hand, it should be handleable without causing fatigue, therefore, the weight of the hand-piece 130 should be kept as low as possible. Hence, one or a plurality of photocells can be used as another alternative for the power supply, the photocells being integrated in the hand-piece 130 and using, for the purpose of generating electric energy, the light existing in the room in question and/or a part of the reflected laser radiation.

The position of the data transmitting means 210 can be chosen such that it is located outside of the numerical aperture (NA) of the light-guide 120. It can be particularly advantageous to position the data transmitting means 210 or LED such that the highest possible percentage of the optical signals of the LED or data transmitting means 210 reflected at the lens system 220, 230 lies within the numerical aperture of the light-guide 120.

Figure 3:
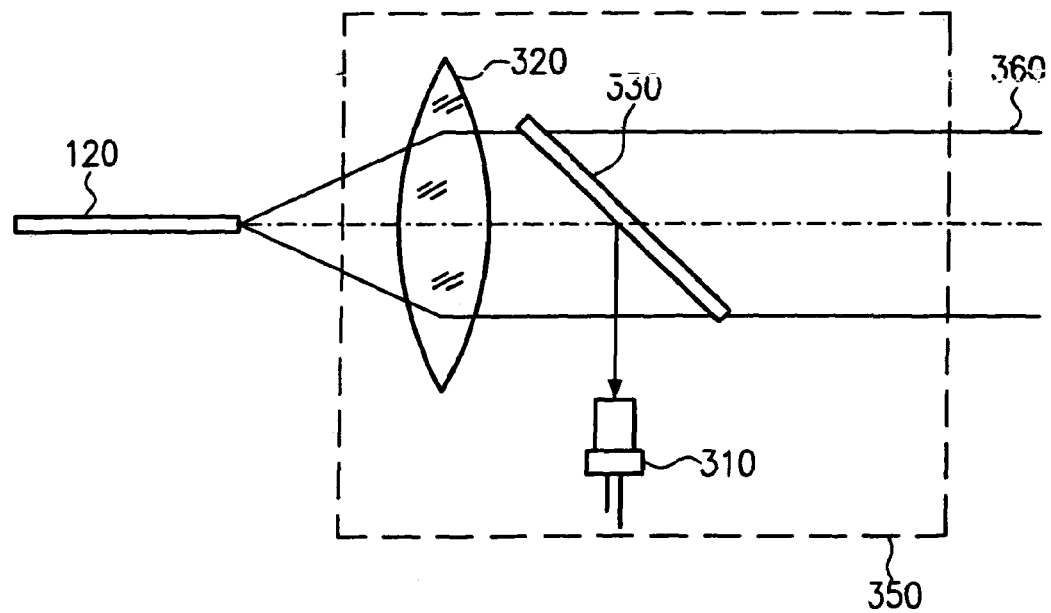
FIG. 3 shows a schematic diagram of the incoupling means and of the light-guide according to exemplary embodiments of the present invention.

FIG. 3 shows a schematic diagram of the incoupling means 350 in accordance with exemplary embodiments of the present invention. The laser radiation 360 generated in the laser unit 110 can be coupled into the light-guide 120 by means of a lens system 320 according to the numerical aperture of the light-guide 120. A first data receiving means 310 can be coupled to the incoupling means via a partially reflecting dielectric mirror 330. The dielectric mirror 330 can be provided at an inclined position in the optical path of the laser so that optical signals conducted from the data transmitting means 210 via the light-guide 120 can be deflected from the optical path of the laser radiation towards the first data receiving means. Since the laser radiation in question is a high-intensity laser radiation, this can also be helpful to avoid damage which might otherwise be caused to the data receiving means.

The dielectric mirror 330 can be provided with such a coating that, with due regard to the inclination of the mirror 330 relative to the optical path of the laser radiation, the reflection of the laser radiation can be minimized so as to keep the losses low on the one hand and so as to protect, on the other hand, the surrounding elements against damage caused by reflections of the intensive laser radiation. The coating of the dielectric mirror 330 can also be optimized in such a way that the reflection is optimized for the spectral region of the optical pulses transmitted by the data transmitting means 210, so that the highest possible percentage of the optical signals can be forwarded to the data receiving means. The transmit power of the data transmitting means 210 and, consequently, the power consumption of the data transmitting means 210 can be reduced in this way.

The electric signals of the data receiving means 310 can be forwarded via an electronic circuit to the display or control unit or to the system controller in the laser unit 110 so as to convert the information transmitted by means of the optical signals into suitable control and adjustment processes. The optical signals of the data transmitting means 210 can be used for transmitting information for adjusting the laser power.

The data receiving means 310 can comprise a commercially available light-sensitive sensor, which is sensitive either to a broad spectral region or only to specific spectral regions. Exemplary embodiments of the invention are not limited to data communication only from the hand-piece 130 to the stationary laser unit 110. They can also be used for data communication from the stationary laser unit 110 to the hand-piece 130.

Figure 4:
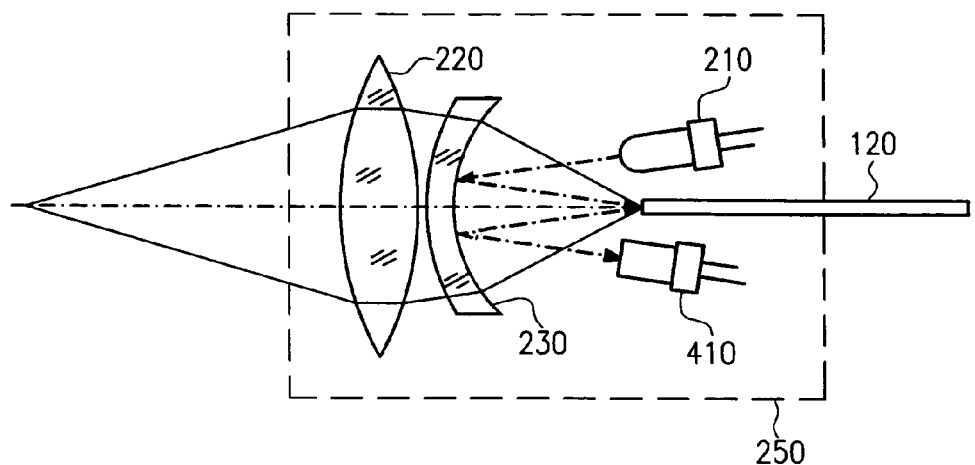
FIG. 4 shows a schematic diagram of the outcoupling means and of the light-guide according to exemplary embodiments of the present invention.

FIG. 4 shows, on the basis of a schematic diagram, the outcoupling means 250 in accordance with exemplary embodiments of the present invention. In such embodiments, the outcoupling means 250 has coupled thereto, in addition to the outcoupling means 250 shown in FIG. 2, a second data receiving means 410. The second data receiving means 410 can be positioned such that the optical signals of the data transmitting means 210 exiting from the light-guide 120 are reflected at the lens system 220, 230 and deflected into the data receiving means 410. In this way, the data receiving means 410 can be prevented from disturbing the optical path of the laser radiation and, in addition, the data receiving means 410 can itself be protected against damage or disturbances caused by direct laser radiation.

The second data receiving means 410 can comprise a commercially available sensor, which, alternatively, can be particularly sensitive to specific frequency regions. In addition, the data receiving means 410 can be supplemented by respective optical filters so that only optical signals of a specific spectral region can arrive at the detection region of the data receiving means 410. The data receiving means 410 can be connected to a suitable display unit in the hand-piece 130, for example, via a hand-piece controller or some other electronic circuit. The information transmitted via the optical signals can be displayed through a display unit of the hand-piece 130.

On the other hand, the data receiving means 410 can convert the optical signals of the data transmitting means 210 into electric signals. The electric signals can be forwarded via an electronic circuit to the display or control unit or to the system controller in the laser unit 110 so as to convert the information transmitted by means of the optical signals into respective control and adjustment processes. Typically, information for controlling the laser power is transmitted by means of the optical signals of the data transmitting means 210. This can essentially facilitate the handling of the laser system 100, since all important information lies within the user's field of vision.

The display unit in the hand-piece 130 can, for example, be used for displaying the respective modes of use and for displaying, in accordance with the use of the laser, a respective spot size of the laser radiation and the laser intensity in question. The information required for this purpose can be transmitted from the laser unit 110 through a respective data transmitting means via the light-guide 120 to the hand-piece 130.

Figure 5:
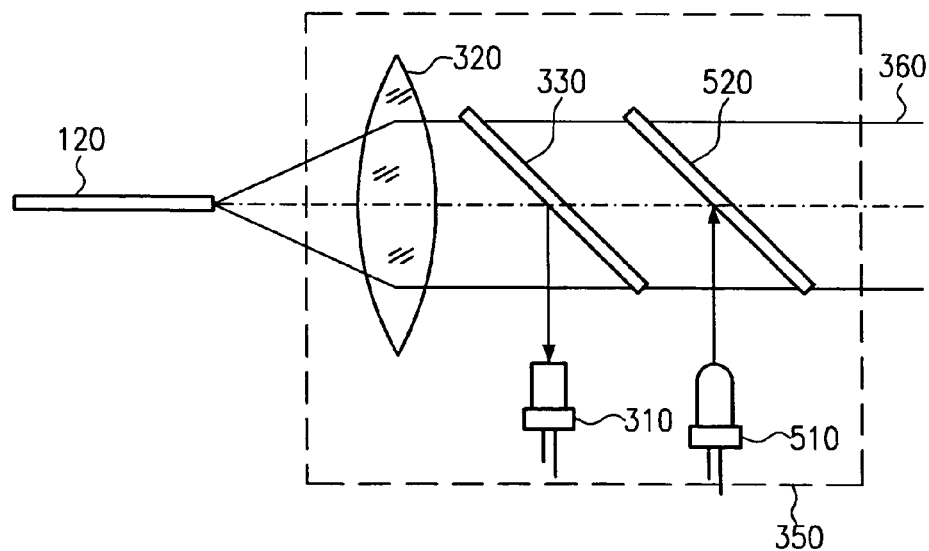
FIG. 5 shows a schematic diagram of the incoupling means and of the light-guide according to exemplary embodiments of the present invention.

FIG. 5 shows the incoupling means 350 in accordance with exemplary embodiments of the present invention. In such embodiments, a data transmitting means 510 is, in addition to the incoupling means 350 shown in FIG. 3, coupled into the laser beam 360 via a dielectric mirror 520. Similar to the dielectric mirror 330, the dielectric mirror 520 can be tilted relative to the radiation direction of the laser radiation so as to couple the optical signals transmitted by the data transmitting means 510 into the optical path of the laser and so as to couple these optical signals into the light-guide 120 via the lens system 320. The dielectric coating of the dielectric mirror 520 can be of such a nature that the reflection losses of the laser radiation can be minimized, whereby the transmission of the laser radiation through the inclined mirror can be optimized. The dielectric coating of the laser mirror 520 can, however, also be optimized in such a way that the dielectric mirror 520 has particularly good reflection properties for the spectral region of the optical signals produced by the data transmitting means 510. Alternatively, also the dielectric mirror 330 as well as the lens system 320 can be used for coupling in the optical signals of the data transmitting means 510.

In exemplary embodiments of the present invention, different spectral regions are used for the optical signals of the data transmitting means 210 and 510. This has the effect that, on the one hand, the dielectric coatings of the optical components used can be optimized with respect to their transmission and reflection behavior, and, on the other hand, the transmit power for the production of the optical signals can be reduced, whereby energy can be saved. In addition, different pulse frequencies, instead of different spectral regions, can be used for the optical signals of the data transmitting means 210 and 510 so as to guarantee a sufficient signal-to-noise ratio between the optical signals produced.

For supplying power to the electronics for the data transmitting means 210 and to the electronics required for the operating means 140, the hand-piece 130 can be provided with a battery or a rechargeable battery. Alternatively, a capacitance-buffered power supply can be used. The hand-piece 130 should fulfill ergonomic requirements on the one hand and, on the other hand, should be handleable without causing fatigue, so the weight of the hand-piece 130 should be kept as low as possible. In accordance with some exemplary embodiments of the invention, an energy-saving electronics can be used so as to keep the weight for the power supply low while still providing reasonable periods of time for the use and the operation of the hand-piece 130.

In accordance with other exemplary embodiments of the present invention, a pilot laser can be used as a data transmitting means 510, where the pilot laser may produce optical signals in the visible spectral region and serve to make the laser radiation produced in the laser unit 110 visible. For transmitting information via optical signals, the pilot laser is typically operated in a pulsed mode. Alternatively, one or a plurality of LEDs can be used for producing optical signals in the data transmitting means 510, where the LEDs are typically operated in a pulsed mode to provide a sufficient signal-to-noise ratio between the optical signals produced and the other optical influences.

By use of a specific pulse frequency for the optical signals, the information transmitted can be differentiated from interference phenomena and from other optical signals. This also can apply to the data transmitting means 210, which, in accordance with some exemplary embodiments of the invention, can use a certain pulse frequency for transmitting the optical signals so that the optical signals will be detected by the data receiving means 310 in a reliable manner and with a suitable signal-to-noise ratio. Using different pulse durations and different frequencies of the optical signals, a reliable bidirectional communication between the laser unit 110 and the hand-piece 130 can be realized via the light-guide 120, which is typically used for transmitting intensive laser radiation.

In accordance with other exemplary embodiments of the present invention, the data receiving means 310 can additionally be used for measuring reemitted radiation, which can originate from the treatment of material with the laser radiation produced. This measurement makes use of the effect that the reemitted radiation produced during the treatment of the material in question is coupled into the light-guide 120 via the lens system 220, 230 in the outcoupling means 250 and that, in the incoupling means 350, it is inevitably also reflected via the dielectric mirror 330 into the data receiving means 310, since the reemitted radiation is, normally a radiation with a broad spectral region. The data receiving means 310 can then measure the intensity of the reemitted radiation and advance it in the form of electric signals to the system controller. The system controller will then be able to adjust the laser power accordingly and to transmit, alternatively, suitable information via the data transmitting means 510 to the hand-piece 130.

When the laser system 100 is used in the field of medicine, exemplary embodiments of the present invention can allow, for example, a variation of the laser spot size via the operating elements 140 in combination with manual or automatic supervision of the laser therapy via the reemitted radiation, without any necessity of providing additional electric cables leading from the laser unit 110 to the hand-piece 130, or susceptible radio or infrared transmitters. As discussed above, the laser spot size can be detected automatically and evaluated via an electronic circuit, whereupon the laser power can be automatically readjusted in a suitable manner.

In accordance with other exemplary embodiments of the present invention, the stationary laser unit 110 can be provided with a charging station for the rechargeable battery in the hand-piece 130. The charging station can be configured such that it is provided with a holder for releasably securing the hand-piece 130 and that both the holder and the hand-piece 130 have integrated therein electric contacts by means of which the rechargeable battery can be charged.

In order to be able to use the hand-piece 130 in a flexible manner in accordance with different exemplary application modes of the laser system 100, the hand-piece 130 can have a modular structural design and, depending on the respective intended use of the laser system 100, elements of the hand-piece 130 can be added, replaced, or removed. Alternatively, the individual elements of the hand-piece 130 can be provided with an identification means, which can be analyzed optically, electronically, or mechanically and which can be read via a reading unit when the elements are mounted to the hand-piece 130. The data can be provided by the identification means being forwarded to the data transmitting means 210 in the hand-piece 130 and used for controlling the hand-piece 130 or the unit for producing laser radiation. In this way, the laser system 100 can adjust itself automatically to various application modes, so that treatment errors caused by incorrect system adjustments can be minimized.

Figure 6:
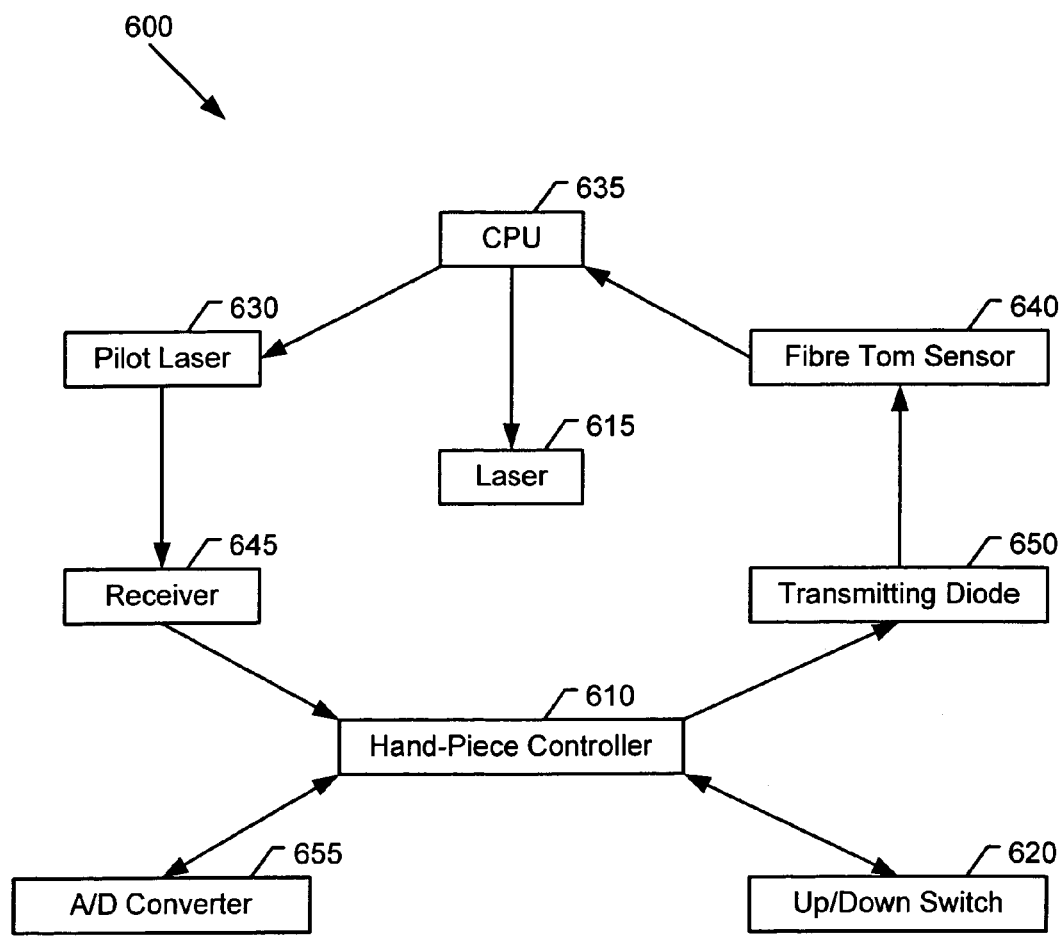
FIG. 6 shows a block diagram of a system controller for controlling the laser power according to exemplary embodiments of the present invention.

FIG. 6 shows a block diagram of a system controller 600 for controlling the laser power according to exemplary embodiments of the present invention. The electronics in the hand-piece 130 can here be provided with an electronic controller ("hand-piece controller 610"). Commands for increasing or reducing the laser power can be transmitted to the hand-piece controller 610 via the operating means 140 in the hand-piece 130 with the keys "up" and "down" of the up/down switch 620. The hand-piece controller 610 transmits the respective electric signals to the data transmitting means 210 in the hand-piece 130, where they are converted into optical signals, coupled into the light-guide 120, and detected in the incoupling means 350 by the data receiving means 310 and converted into electric signals. Electric signals are transmitted to the system controller 600, which reduces or increases the power of the laser 615.

The system controller 600 can transmit the current laser power value by means of electric pulses to the pilot laser 630, which can transmit corresponding optical signals via the light-guide 120 to the data receiving means 410 in the hand-piece 130. The optical signals can be detected in the hand-piece 130 and forwarded in the form of electric signals to the hand-piece controller 610. There, for example, the current laser power value can be displayed in the display unit of the hand-piece 130. Alternatively, the system controller 600 in the laser unit 110 can inform the hand-piece controller 610 also of the intensity of the measured reemitted radiation. The laser power is typically detected directly at the end of the fiber, since this is a reliable method of determining the laser power emitted. The laser power can additionally be displayed in the display unit of the hand-piece 130. Depending on the case in question, display of the values may be effected continuously or only if a specific value has been exceeded.

Figure 7:
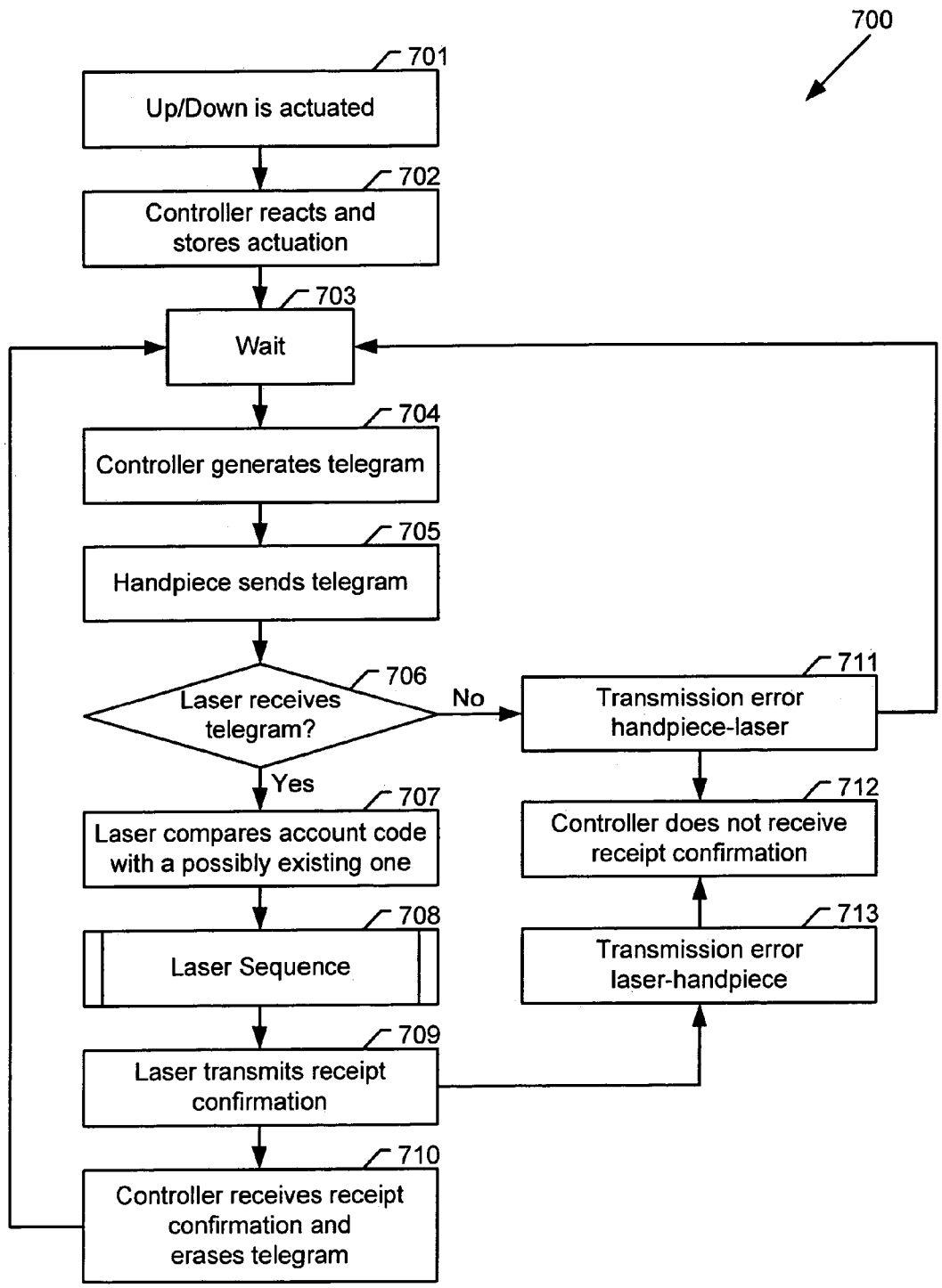
FIG. 7 shows a flowchart for the schematic sequence of data communication steps between the stationary unit of the laser system and the hand-piece according to exemplary embodiments of the present invention.
Figure 8:
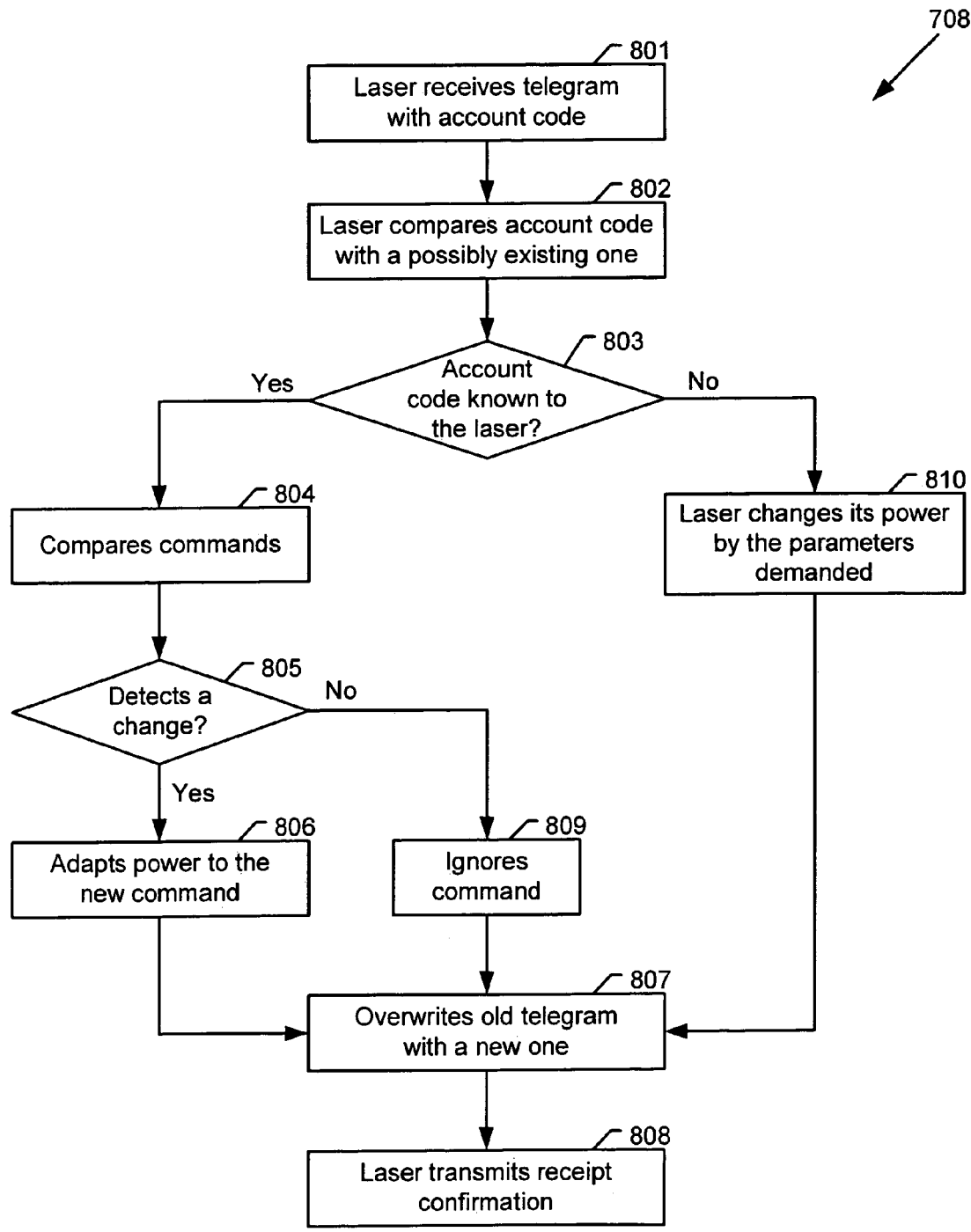
FIG. 8 shows a further flowchart for the schematic sequence of data communication steps between the stationary unit of the laser system and the hand-piece according to exemplary embodiments of the present invention.

FIGS. 7 and 8 show flowcharts for a schematic sequence of data communication steps between the stationary unit of the laser system and the hand-piece according to exemplary embodiments of the present invention as described with respect to FIG. 6. By actuating the operating means 140, respective electric signals can be transmitted to the hand-piece controller 610 (step 701). The hand-piece controller 610 can evaluate the electric signals and store them in an intermediate memory (step 702). Following this, the hand-piece controller 610 can wait for a system inquiry from the system controller 600 of the laser unit 110 by means of the pilot laser 630 (step 703). If the laser system 100 controller makes an inquiry, the hand-piece controller 610 can generate a so-called telegram (step 704) and send the telegram to the system controller 600 through the data transmitting means 210 provided in the hand-piece 130 and through the light-guide 120 (step 705). When the system controller 600 receives the telegram (step 706), it can compare an identification number, which is contained in the telegram and which is also referred to as account code, with possibly existing identification numbers (step 707). If the so-called account code is known to the system controller 600, the control commands contained in the telegram can be compared with those contained in the telegram which are already known (routine 708). If changes are detected in the control commands, the current control commands will be executed and the telegram with the identical account code will be overwritten (routine 708).

If the account code of the telegram sent is not yet known to the system controller 600, the control command check can be skipped and the respective execution of the control commands as well as the adjustment of the necessary parameters can be carried out immediately (routine 708). When the control commands for adjusting the new parameters have been executed, the system controller 600 can transmit a receipt confirmation to the hand-piece controller 610 by means of the pilot laser 630 (step 709). The hand-piece controller 610 can receive the receipt confirmation and erase the telegram in the intermediate memory (step 710).

Such a system controller 600 can be used for controlling not only parameters of the therapy laser, such as, for example, laser power and pulse duration, but also optical components, such as the incoupling means 350 and the outcoupling means 250, so as to adapt the laser system 100 to the application modes in question.

The present invention is not limited to exemplary embodiments described above, and can also include various combinations of the above described exemplary embodiments. In addition, the present invention is not limited to the field of medical applications, and it can also be used in an equivalent manner in the fields of material processing and material analysis.

While the invention has been described with respect to exemplary embodiments constructed in accordance therewith, it will be apparent to those skilled in the art that various modifications, variations and improvements of the present invention may be made in the light of the above teachings and within in the purview of the appended claims without departing from the spirit and intended scope of the invention. In addition, those areas in which it is believed that those of ordinary skill in the art of familiar have not been described herein in order not to unnecessarily obscure the invention described herein. Accordingly, it is to be understood that the invention is not to be limited by any of the exemplary embodiments, but only by the scope of the appended claims.

What is claimed is:

1. A medical laser system, comprising:
   a laser unit configured to produce laser radiation for medical treatment;
   a light-guide having a first end and a second end;
   an incoupling device configured to incouple the laser radiation from the laser unit into the first end of the light-guide;
   an outcoupling device comprising at least one lens configured to outcouple the laser radiation from the second end of the light-guide;
   a first data transmitter associated with the incoupling device and configured to provide first optical signals which are incoupled into the first end of the light-guide via the incoupling device;
   a first data receiver associated with the outcoupling device and configured to receive the first optical signals from the second end of the light-guide;
   a second data transmitter associated with the outcoupling device and configured to provide second optical signals which are reflected into the second end of the light-guide via the lens of the outcoupling device; and
   a second data receiver associated with the incoupling device and configured to receive the second optical signals from the first end of the light-guide.

2. The laser system according to claim 1, wherein the first data transmitter is coupled to the incoupling device.

3. The laser system according to claim 1, wherein the second data receiver is coupled to the incoupling device.

4. The laser system according to claim 1, wherein the first data receiver is coupled to the outcoupling device.

5. The laser system according to claim 1, wherein the second data transmitter is coupled to the outcoupling device.

6. The laser system according to claim 1, wherein a wavelength of the first optical signals is different than a wavelength of the second optical signals.

7. The laser system according to claim 1, wherein a wavelength of the laser radiation is different than a wavelength of each of the first optical signals and the second optical signals.

8. The laser system according to claim 1, wherein the first optical signals comprise information concerning a status of the laser system.

9. The laser system according to claim 1, wherein the second optical signals comprise information concerning the status of the laser system.

10. The laser system according to claim 1, wherein each of the first optical signals and the second optical signals comprise at least one of information for controlling the laser unit, information for producing laser radiation, information for controlling the incoupling device, and information for controlling the outcoupling device.

11. The laser system according to claim 1, wherein the first optical signals comprise information for controlling a power level of the laser radiation.

12. The laser system according to claim 1, wherein the outcoupling device further comprises a lens system for focusing the laser radiation, the lens system comprising the at least one lens configured to outcouple the laser radiation from the second end of the light-guide.

13. The laser system according to claim 1, wherein the first data transmitter comprises a light emitting diode configured to emit the first optical signals.

14. The laser system according to claim 13, wherein the light emitting diode is configured to emit the first optical signals in a blue spectral range.

15. The laser system according to claim 1, wherein the second data transmitter comprises a light emitting diode configured to emit the second optical signals.

16. The laser system according to claim 15, wherein the light emitting diode is configured to emit the second optical signals in a blue spectral range.

17. The laser system according to claim 1, wherein the lens comprises a dielectric coating.

18. The laser system according to claim 1, wherein the incoupling device comprises a mirror with a dielectric coating, wherein the mirror is transparent to the laser radiation and is configured to reflect the second optical signals.

19. The laser system according to claim 1, wherein the first optical signals have specific pulse durations which make them distinguishable from the second optical signals and other interfering signals.

20. The laser system according to claim 1, wherein the second optical signals have specific pulse durations which make them distinguishable from the first optical signals and other interfering signals.

21. The laser system according to claim 1, wherein the second data receiver is further configured to detect additional optical signals.

22. The laser system according to claim 1, wherein the first data receiver is further configured to detect additional optical signals.

23. The laser system according to claim 1, wherein the first data transmitter comprises a pilot laser configured to indicate the focus of the laser radiation.

24. The laser system according to claim 1, further comprising a means for measuring reemitted radiation, wherein the reemitted radiation is produced when material is treated by the laser radiation.

25. The laser system according to claim 1, wherein the second data receiver is further configured to detect reemitted radiation, wherein the reemitted radiation is produced when material is treated by the laser radiation.

26. The laser system according to claim 1, further comprising a hand-piece connected via the light-guide to the laser unit.

27. The laser system according to claim 26, wherein the outcoupling device, the second data transmitter, and the second data receiver are integrated in the hand-piece.

28. The laser system according to claim 26, wherein the hand-piece comprises an operating device configured to provide electric signals that control the laser unit and to forward the electric signals to the second data transmitter to be converted to the second optical signals.

29. The laser system according to claim 26, wherein the hand-piece comprises a display unit operable to display information received via the first data receiving means.

30. The laser system according to claim 26, wherein the hand-piece further comprises:
   an operating device configured to provide electric signals that control the laser unit and to forward the electric signals to the second data transmitter to be converted to the second optical signals;
   a display unit operable to display information received via the first data receiving means; and
   a rechargeable battery configured to supply power to the second data transmitter, the first data receiver, the operating device, and the display unit.

31. The laser system according to claim 30, further comprising a charging device coupled to the laser unit, the charging device comprising a holder configured to detachably fasten to the hand-piece, and wherein each of the holder and the hand-piece comprises at least one electric contact configured to charge the rechargeable battery.

32. The laser system according to claim 26, further comprising photocells configured to supply power to the second data, transmitter and the first data receiver, wherein the photocells are integrated in the hand-piece and are further configured to use at least one of conventional light and reflected laser radiation to generate electric energy.

33. The laser system according to claim 26, wherein the hand-piece comprises a modular structural design with interchangeable elements that are mountable to the hand-piece depending on the respective intended use of the laser system.

34. The laser system according to claim 33, wherein each of the interchangeable elements of the hand-piece comprises identification information that is arranged to be identified via a reading unit in the hand-piece when the the respective element is mounted to the hand-piece, whereby the identification information is forwarded to the second data transmitter and used for controlling at least one of the hand-piece and the laser unit.

35. The laser system according to claim 33, wherein the hand-piece comprises a modular structural design with interchangeable elements that are independently mountable to the hand-piece depending on the respective intended use of the laser system, each of the interchangeable elements of the hand-piece comprising identification information that is arranged to be identified via a reading unit in the hand-piece when the respective element is mounted to the hand-piece, whereby the identification information is forwarded to the second data transmitter and used for controlling at least one of the hand-piece and the laser unit.

36. The laser system according to claim 1, wherein a spectral sensitivity of the first data receiver is different than a spectral sensitivity of the second data receiver.

* * * * *

UNITED STATES PATENT AND TRADEMARK OFFICE
CERTIFICATE OF CORRECTION

PATENT NO. : 7,006,749 B2
DATED : February 28, 2006
INVENTOR(S) : Wolfgang Illich et al.

Page 1 of 1

It is certified that error appears in the above-identified patent and that said Letters Patent is hereby corrected as shown below:

Title page,
Item [30], Foreign Application Priority Data, "102 36 175" should read
-- 102 36 175.4 --.

Column 14,
Line 9, "second data, transmitter" should read -- second data transmitter --.

Signed and Sealed this

Sixth Day of June, 2006

JON W. DUDAS
*Director of the United States Patent and Trademark Office*